(12) United States Patent
Iwasaki et al.

(10) Patent No.: US 7,776,414 B2
(45) Date of Patent: Aug. 17, 2010

(54) INFUSION CONTAINER WITH MULTIPLE CHAMBERS

(75) Inventors: Toshiharu Iwasaki, Kawasaki (JP);
Masataka Kotani, Yokohama (JP);
Kiyokazu Ishiwatari, Miura-gun (JP);
Katsuyuki Yoshikawa, Ichihara (JP)

(73) Assignee: Hosokawa Yoko Co., Ltd., Tokyo (JP)

( * ) Notice: Subject to any disclaimer, the term of this patent is extended or adjusted under 35 U.S.C. 154(b) by 968 days.

(21) Appl. No.: 10/508,481

(22) PCT Filed: Mar. 27, 2003

(86) PCT No.: PCT/JP03/03854

§ 371 (c)(1),
(2), (4) Date: May 31, 2005

(87) PCT Pub. No.: WO03/082549

PCT Pub. Date: Oct. 9, 2003

(65) Prior Publication Data

US 2005/0221034 A1      Oct. 6, 2005

Related U.S. Application Data

(60) Provisional application No. 60/412,796, filed on Sep. 24, 2002.

(30) Foreign Application Priority Data

Mar. 28, 2002  (JP)  ............................. 2002-093177
Jan. 31, 2003  (JP)  ............................. 2003-023436

(51) Int. Cl.
*B65D 25/08*  (2006.01)
*A61B 19/00*  (2006.01)

(52) U.S. Cl. ...................... 428/35.4; 428/34.1; 206/0.5; 206/219; 604/410; 604/416

(58) Field of Classification Search ................. 428/156, 428/343, 352, 354; 277/602; 385/68
See application file for complete search history.

(56) References Cited

U.S. PATENT DOCUMENTS 5,076,040 A * 12/1991 Davis .......................... 53/551

(Continued)

FOREIGN PATENT DOCUMENTS

EP         0920849 A      6/1999

(Continued)

*Primary Examiner*—Rena L Dye
*Assistant Examiner*—Ellen S Wood
(74) *Attorney, Agent, or Firm*—Sughrue Mion, PLLC

(57) ABSTRACT

The present invention has an object to provide an infusion container with multiple chambers, where the peel strength of the boundary portion between one and another of multiple medicament chambers is stabilized irrespective of the construction material and structure of the film. The present invention provides an infusion container 10 with multiple chambers, which is formed from a thermoplastic resin film and has a plurality of medicament chambers 11 and 12 for housing medicaments, wherein the medicaments chambers 11 and 12 are liquid-tightly sealed by a peelable weak seal part 15, the weak seal part 15 is formed to have a plurality of melt-bonding parts different in the melt-bonding strength, the strong melt-bonding part having a largest melt-bonding strength among these melt-bonding parts is dispersed and distributed in the weak seal part 15, and the total occupied area of the strong melt-bonding part is less than 25% of the area of the weak seal part 15.

12 Claims, 8 Drawing Sheets

U.S. PATENT DOCUMENTS

| | | | |
|---|---|---|---|
| 5,871,607 A * | 2/1999 | Hamilton et al. | 156/221 |
| 6,186,998 B1 * | 2/2001 | Inuzuka et al. | 604/410 |
| 6,468,377 B1 * | 10/2002 | Sperko et al. | 156/229 |
| 7,040,483 B2 * | 5/2006 | Inuzuka et al. | 206/219 |

FOREIGN PATENT DOCUMENTS

| | | | |
|---|---|---|---|
| EP | 1288141 A | | 3/2003 |
| JP | 2-4671 A | | 1/1990 |
| JP | H3-85038 | | 8/1991 |
| JP | 08-24314 A | | 1/1996 |
| JP | 11-169432 A | | 6/1999 |
| JP | 11169432 A | * | 6/1999 |
| JP | 2000-14746 A | | 1/2000 |

* cited by examiner ary portion.
INFUSION CONTAINER WITH MULTIPLE CHAMBERS

CROSS-REFERENCE TO RELATED APPLICATIONS

This application claims the benefit of U.S. Provisional Application No. 60/412,796, filed on Sep. 24, 2002, which is hereby incorporated by reference, and is based on Japanese Patent Application No. 2002-093177 filed on Mar. 28, 2002 and Japanese Patent Application No. 2003-023436 filed on Jan. 31, 2003, which are hereby incorporated by reference.

TECHNICAL FIELD

The present invention relates to an infusion container with multiple chambers, where a plurality of medicaments can be separately housed and these medicaments can be easily mixed on use, and also relates to a production method thereof.

BACKGROUND ART

As a practical treatment, a plurality of medicaments are mixed and administered to a patient, for example, a vitamin compound or the like is mixed in physiological saline and the solution is injected or instilled to a patient. In the case of mixing a plurality of medicaments as such, if these are previously mixed, degeneration may occur depending on the kind of the medicament. Therefore, an infusion container with multiple chambers is being used, where a plurality of medicaments having possibility of degeneration can be separately housed and can be mixed immediately before use. In some infusion containers with multiple chambers, the body is formed of a thermoplastic resin film such as polyolefin.

Such an infusion container with multiple chambers, which is formed of a thermoplastic resin film, is necessary to satisfy the requirement that the boundary portion between medicament chambers is liquid-tightly sealed in the stage before mixing a plurality of medicaments but on mixing the plurality of medicaments, the boundary portion can be easily peeled apart to open the path between chambers and the medicaments can be rapidly mixed. Therefore, a large number of studies have been made on the method for forming the boundary portion.

For example, JP-A-2-4671 (the term "JP-A" as used herein means an "unexamined published Japanese patent application") and JP-A-2000-14746 disclose a technique of forming the portion participating in the adhesion from a specific material so as to form a readily peelable boundary portion. Furthermore, JP-A-11-169432 describes a method of coating an easily peelable coating agent on the inner surface of the boundary portion and thereby facilitating the peeling.

On the other hand, JP-A-8-24314 discloses a technique where two bars each with a seal edge having a specific shape are used in combination as a heat seal bar for use at the sealing of the boundary portion and the film is sandwiched therebetween while precisely controlling the positions of these seal edges, so that the boundary portion can have an appropriate peel strength.

However, the techniques disclosed in JP-A-2-4671 and JP-A-2000-14746 have a problem that since an easily peelable boundary portion is formed, the portion must be composed of multiple layers but a single layer film cannot be applied and the production of film costs highly. Also, the technique described in JP-A-11-169432 has a problem that a specific coating agent is necessary and the production step or production cost increases.

In the method disclosed in JP-A-8-24314, it is not essential to form a film having a multilayer structure or use a coating agent, but seal edges of heat seal bars for sealing the boundary portion must be aligned and if these positions are misaligned, the peel strength of the formed boundary portion is greatly dispersed among infusion containers each having multiple chambers. Furthermore, in the case where the heat seal bar has a narrow perforation pitch, the positions are very difficult to align and even if the heat seal temperature is maintained at a fixed temperature, the peel strength may be dispersed among infusion containers each having multiple chambers. It has been demanded to stably produce an infusion container with multiple chambers, having a desired peel strength.

DISCLOSURE OF INVENTION

The present invention has been made under these circumstances and an object of the present invention is to provide an infusion container with multiple chambers, where the peel strength of the boundary portion between one and another of multiple medicament chambers is stabilized irrespective of the construction material and structure of the film. Another object of the present invention is to provide a method capable of easily producing such an infusion container having multiple chambers with good productivity.

The present inventors have found that when the weak seal part for partitioning multiple medicament chambers from each other is formed to have a plurality of melt-bonding parts different in the melt-bonding degree and the total occupied area of the strong melt-bonding part having a largest melt-bonding strength among these melt-bonding parts is controlled, the above-described objects can be attained. The present invention has been accomplished based on this finding. The term "large melt-bonding strength" as used herein means that the power necessary for peeling apart the portion which is melt-bonded and sealed is large.

In addition, the term "melt-bonding" as used in the present invention means adhering by pressing while heating, and not only indicates the condition that thermoplastic resin films are melted and are completely united therewith, so that the boundary thereof is unclear, but also includes the condition that the boundary between the thermoplastic resin films is observed, so long as a liquid-tight seal is maintained.

The infusion container with multiple chambers of the present invention is formed from a thermoplastic resin film and has multiple medicament chambers for housing medicaments, wherein at least a part of the peripheral edge of the infusion container with multiple chambers is liquid-tightly sealed by a strong seal part, respective medicament chambers are liquid-tightly sealed by a peelable weak seal part, the weak seal part is formed to have a plurality of melt-bonding parts different in the melt-bonding strength, the strong melt-bonding part having a largest melt-bonding strength among these melt-bonding parts is dispersed and distributed in the weak seal part and the total occupied area of the strong melt-bonding part is less than 25% of the area of the weak seal part.

The method for producing an infusion container with multiple chambers of the present invention is a method for producing an infusion container with multiple chambers, which has multiple medicament chambers for housing medicaments and in which respective medicament chambers are liquid-tightly sealed by a peelable weak seal part, the method comprising a weak seal step of sandwiching two superposed thermoplastic resin films from both sides using two heat seal bars to form a weak seal part having a plurality of melt-bonding parts different in the melt-bonding strength, wherein the weak seal step is performed such that the total occupied area of the

BEST MODES FOR CARRYING OUT THE INVENTION

The present invention is described in detail below.

First Embodiment

Figure 1:
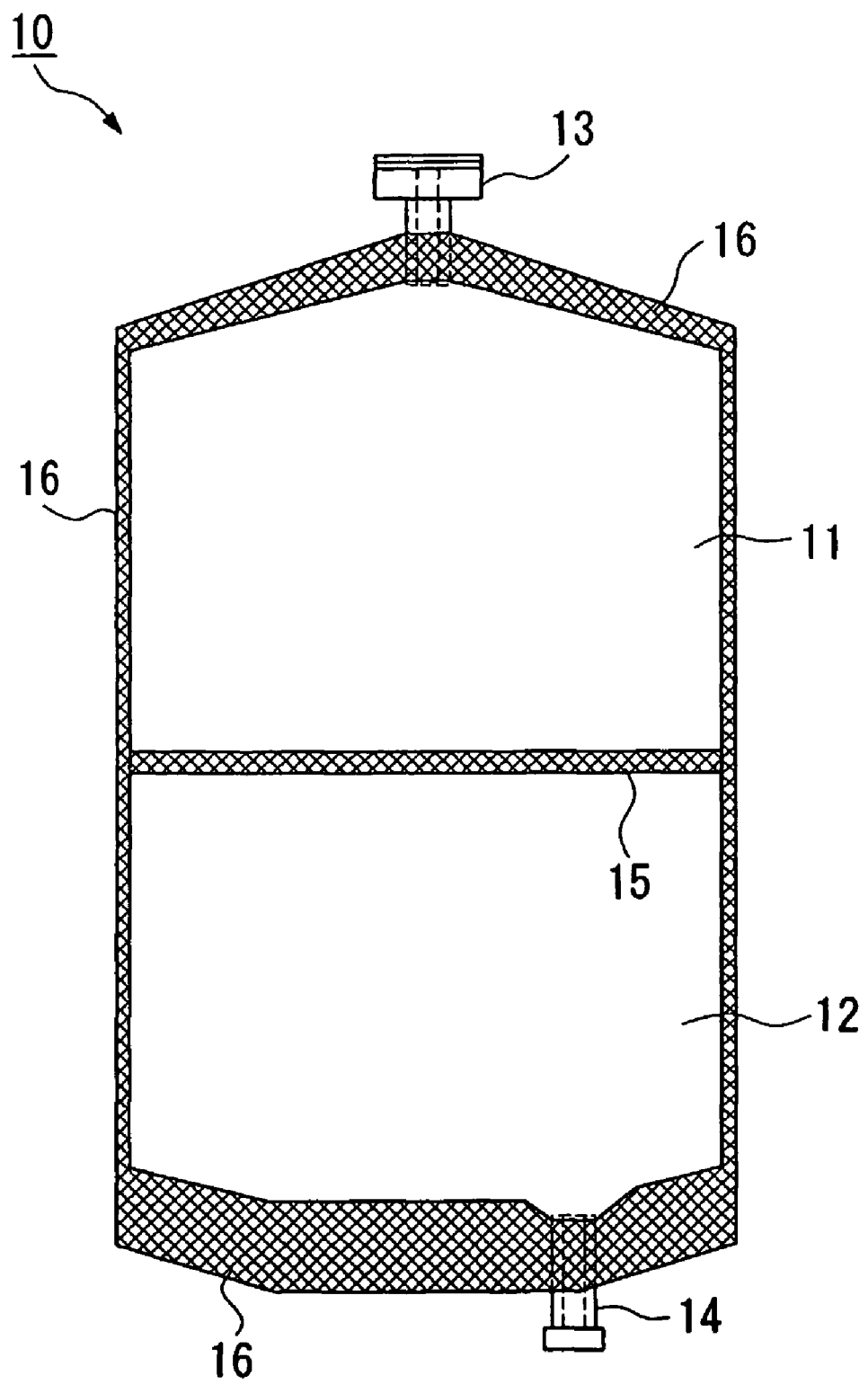
FIG. 1 is a plan view showing one example of the infusion container with multiple chambers of the present invention.

FIG. 1 is one example of the infusion container with multiple chambers of the present invention, which is formed from a thermoplastic resin film and has two medicament chambers 11 and 12 where a medicament will be filled. In the infusion container 10 with multiple chambers of this example, one medicament chamber 11 is connected by a medicament charging part 13 and another medicament chamber is connected by a medicament inlet/outlet part 14 for charging a medicament thereinto and on administering the medicament to a patient, discharging the medicament from the chamber.

In this infusion container 10 with multiple chambers, those two medicament chambers 11 and 12 are separated by a liquid-tight weak seal part 15. After medicaments are filled in respective medicament chambers 11 and 12, the weak seal part 15 is heat-sealed such that the portion can be peeled apart by externally applying a force to at least either one of the medicament chambers 11 and 12 and the medicaments can be rapidly and easily mixed with each other on demand.

On the other hand, the peripheral edge of this infusion container 10 with multiple chambers is liquid-tightly closed by a strong seal part 16 which is not peeled apart even when a force is externally applied to the medicament chamber 11 or 12. In this part, the thermoplastic resin films are heat-sealed and strongly melt-bonded. In this example, the strong seal part 16 is formed throughout the peripheral edge of the infusion container 10 with multiple chambers, however, for example, in the case of using a cylindrical thermoplastic resin film as the material, the strong seal part 16 may be formed only on both edges in the longitudinal direction of film (in the Figure, upper and lower end parts). The strong seal part 16 is not always necessary to be formed on the entire peripheral edge.

The weak seal part 15 of the infusion container 10 with multiple chambers of this example is formed by sandwiching two superposed thermoplastic resin films from both surface sides by two heat seal bars each having a specific seal edge formed on the seal surface, which is described in detail later. As partially shown in the enlarged plan view of FIG. 2, this part is formed to have three melt-bonding parts different in the melt-bonding strength, namely, a strong melt-bonding part 15a, a medium melt-bonding part 15b and a weak melt-bonding part 15c.

The strong melt-bonding part 15a having a highest melt-bonding strength among these melt-bonding parts has a nearly square form and almost uniformly dispersed and distributed in the weak seal part 15. The weak melt-bonding part 15c having a lowest melt-bonding strength in the weak seal part 15 has a nearly square form larger than the strong melt-bonding part 15a and is almost uniformly dispersed and distributed in the weak seal part 15. The medium melt-bonding part 15b having a melt-bonding strength between the strong melt-bonding part 15a and the weak melt-bonding part 15c has a nearly rectangular form and similarly, almost uniformly dispersed and distributed in the weak seal part 15. Among the strong melt-bonding part 15a, the medium melt-bonding part 15b and the weak melt-bonding part 15c, the thickness of the strong melt-bonding part 15a is smallest and the thickness of the weak melt-bonding part 15c is largest.

Furthermore, the strong melt-bonding part 15a having a highest melt-bonding strength among these three kinds of melt-bonding parts is formed such that the total occupied area thereof is less than 25% of the entire area of the weak seal part 15.

Therefore, the peel strength of the weak seal part 15 is appropriately controlled and the power necessary for opening the part, namely, the opening strength also becomes appropriate, so that the weak seal part thus formed can maintain the liquid-tight separation between the medicament chambers 11 and 12 at an ordinary time but when a force is externally applied to the medicament chamber 11 or 12, can be easily peeled apart and opened.

If the total of occupied areas of respective strong melt-bonding parts 15a in the weak seal part 15 is 25% or more, the opening strength is excessively large and the weak seal part 15 cannot be easily peeled apart on demand, whereas if it is less than 0.01%, the opening strength is small and the weak seal part may be peeled apart by an impact or the like. Accordingly, the total of occupied areas of respective strong melt-bonding parts 15a is preferably from 0.01 to 25%, more preferably from 0.01 to 15%, still more preferably from 0.05 to 10%.

In the infusion container 10 with multiple chambers of this example, respective strong melt-bonding parts 15a are distributed such that the average of spaces between respective adjacent strong melt-bonding parts 15a, namely, the average space A, and the average of distances between respective adjacent strong melt-bonding parts 15a, namely, the average distance B, satisfy the following formula (1):

$$B < 2A \quad (1)$$

Figure 3:
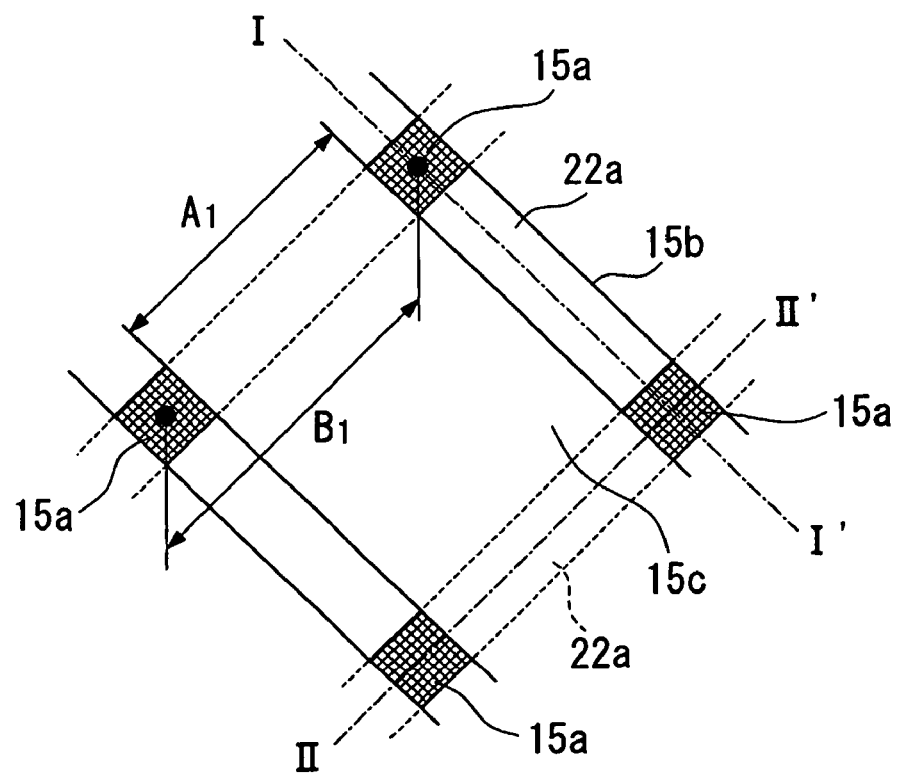
FIG. 3 is a further partially enlarged plan view showing the weak seal part of the infusion container with multiple chambers of FIG. 1.

Here, the distance between adjacent strong melt-bonding parts 15a is, as shown by the symbol $B_1$ in FIG. 3, a distance between centroids of adjacent strong melt-bonding parts 15a and the average distance B is an average of these distances. Also, the space between adjacent strong melt-bonding parts 15a is, as shown by the symbol $A_1$, a distance from the distal end of one strong melt-bonding part 15a to the distal end of another strong melt-bonding part 15a on a line connecting centroids of adjacent strong melt-bonding parts 15a and the average space A is an average of these distances.

When the strong melt-bonding part 15a is distributed to satisfy formula (1), the opening strength of the weak seal part 15 can be more unfailingly and easily controlled. Furthermore, when the average distance B is 1 mm or more, preferably 1.5 mm or more, more preferably 2 mm or more, the opening strength of the weak seal part 15 can be more unfailingly and easily controlled. The upper limit of the average distance B is preferably 10 mm, more preferably 5 mm. If $B \geq 2A$, the opening strength becomes too large and even when a force is applied to the medicament chamber 11 or 12 on demand, the weak seal part 15 may not be easily opened.

In this example, each strong melt-bonding part 15 has a nearly square plane having one side length of almost 0.2 mm (area: 0.04 mm$^2$), the average space A is 1.8 mm, the average distance B is 2 mm and the total occupied area of the strong melt-bonding part is 1%. In the case where each strong melt-bonding part 15a has such a plane, each area is preferably 1 mm$^2$ or less, more preferably 0.5 mm$^2$ or less.

According to this infusion container 10 with multiple chambers, the total of occupied areas of respective strong melt-bonding parts 15a in the weak seal part 15 is less than 25%, so that the peal strength of the weak seal part 15 can be appropriately controlled to give a proper opening strength and even when the thermoplastic resin film used is a single layer film of, for example, polyolefin resin having crystallinity and the peel strength thereof is relatively difficult to control, the peel strength of the formed weak seal part 15 can be controlled, as a result, the opening strength can be easily controlled to fall in an appropriate range without fail. The method for measuring the opening strength is described later in Examples.

In the case of heat-sealing a polyolefin resin film having crystallinity, the sealing is usually performed at a temperature near the melting point of this resin. However, in the vicinity of the melting point, melting of the crystal abruptly proceeds and even by a slight change in the heat seal temperature, the peel strength of the formed weak seal part 15 may fluctuate. If the peel strength fluctuates as such, the opening strength of the weak seal part 15 may be dispersed among individual infusion containers 10 each having multiple chambers and an infusion container with multiple chambers may not be produced to have a stable performance. However, when the area of the strong melt-bonding part 15a is controlled as above, even if the thermoplastic resin film used is a single layer film having crystallinity and is sealed at a temperature near the melting point thereof and also the heat sealing temperature is slightly changed, the dispersion in the peel strength of the weak seal part 15 can be suppressed to the minimum and an infusion container 10 with multiple chambers having a fixed opening strength can be stably produced.

The thermoplastic resin film for use in the infusion container 10 with multiple chambers of this example is preferably a polyolefin resin because this is inexpensive and excellent in the transparency and flexibility. Examples thereof include polyethylene-base resins such as high-density polyethylene, medium-density polyethylene, high-pressure low-density polyethylene, low-density polyethylene, linear low-density polyethylene and ethylene-vinyl acetate copolymer; olefin-base elastomers such as ethylene-butadiene random copolymer; polypropylene-base resins such as polypropylene, ethylene-propylene random copolymer and α-olefin-propylene random copolymer; and a mixture thereof. According to this infusion container 10 with multiple chambers, a specific resin needs not be selected and used for forming the weak seal part 15 as described above and therefore, a resin usable as the thermoplastic resin film in the medical field can be used without any particular limitation. Also, a film comprising a vinyl chloride, an ethylene-vinyl acetate copolymer, a polyether sulfone, a cyclic polyolefin, a cyclic polyolefin copolymer, a styrene-base elastomer such as hydrogenated styrene ethylene butadiene copolymer, a mixture of two or more of these resins, or a mixture of such a resin with the above-described polyolefin-base resin can be used. These resins may be partially crosslinked for the purpose of elevating heat resistance or the like.

The thermoplastic resin film used may be a single layer film composed of one kind of film or a multilayer film obtained by laminating multiple kinds of films. In the case of a single layer film, a film comprising a linear low-density polyethylene, an ethylene propylene random copolymer, an ethylene propylene block copolymer, or a mixture of a polypropylene-base resin and a styrene-base elastomer is preferred because of excellent transparency and flexibility. In the case of a multilayer film, examples thereof include films comprising, from the outer side of the infusion container with multiple chambers, high-density polyethylene/linear low-density polyethylene, medium-density polyethylene/low-density polyethylene/high-density polyethylene, or high-density polyethylene/low-density polyethylene/high-density polyethylene.

In the multilayer film, the inner layer may be composed of a resin composition which enables easy peeling.

The method for producing the film is not particularly limited and examples thereof include production methods using T-die casting, water-cooling inflation molding, blow molding or lamination molding. In view of transparency, T-die casting and water-cooling inflation molding are preferred.

The thermoplastic resin film used has a thickness of 5 to 1,000 μm, preferably on the order of 50 to 500 μm.

Figure 4:
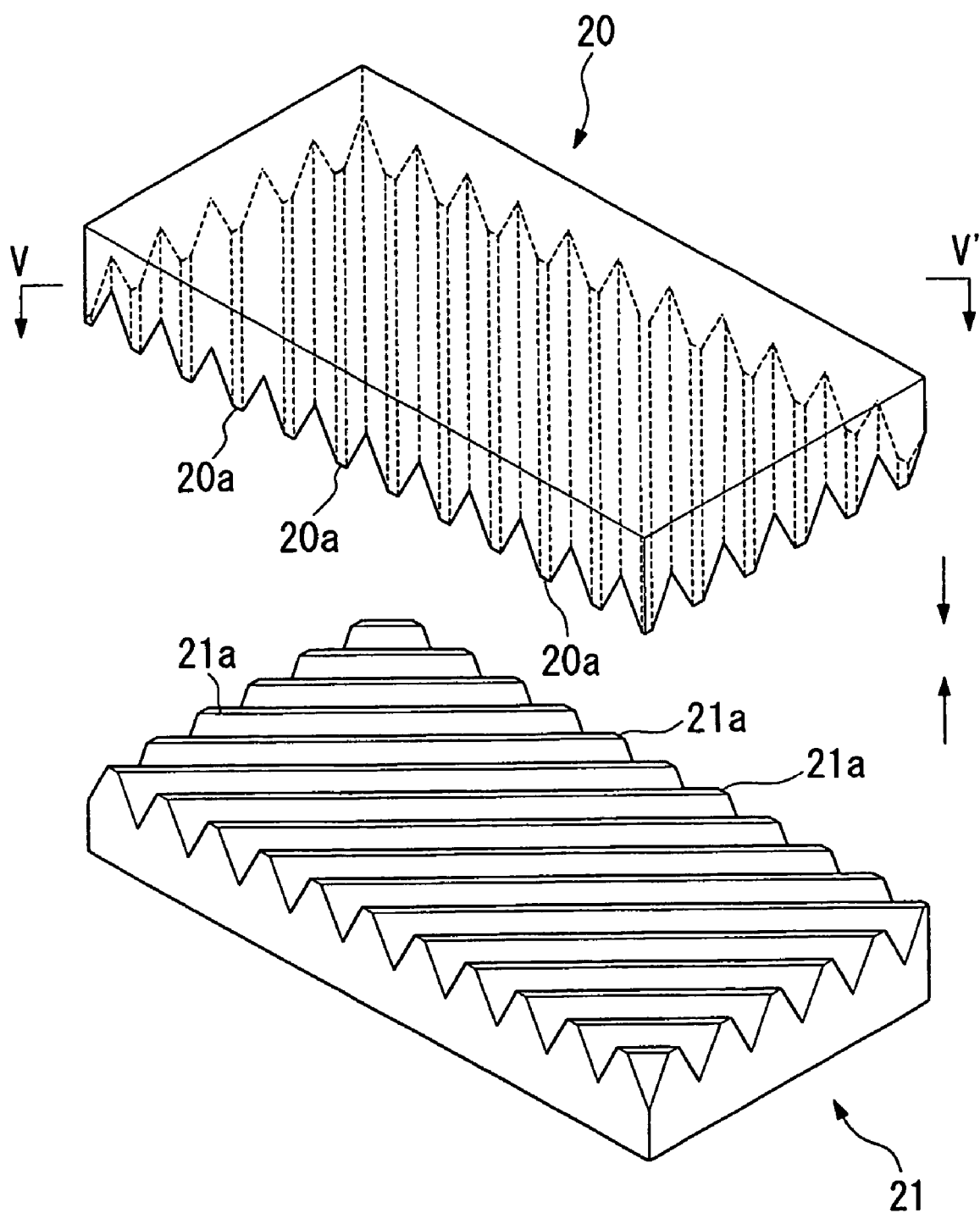
FIG. 4 is a perspective view of the heat seal bar used for forming the weak seal part of the infusion container with multiple chambers of FIG. 1.

The weak seal part 15 of the infusion container 10 with multiple chambers can be formed by sandwiching superposed two thermoplastic resin films from both surface sides using two heat seal bars 20 and 21 having seal edges 20a and 21a, respectively, on the seal surface as shown in FIG. 4. As for the superposed two thermoplastic resin films, two sheets in the film form may be superposed or a film previously molded into a cylindrical form may be used. In addition to these two thermoplastic resin films, a new film may be inserted and sealed in the weak seal part 15.

Figure 5:
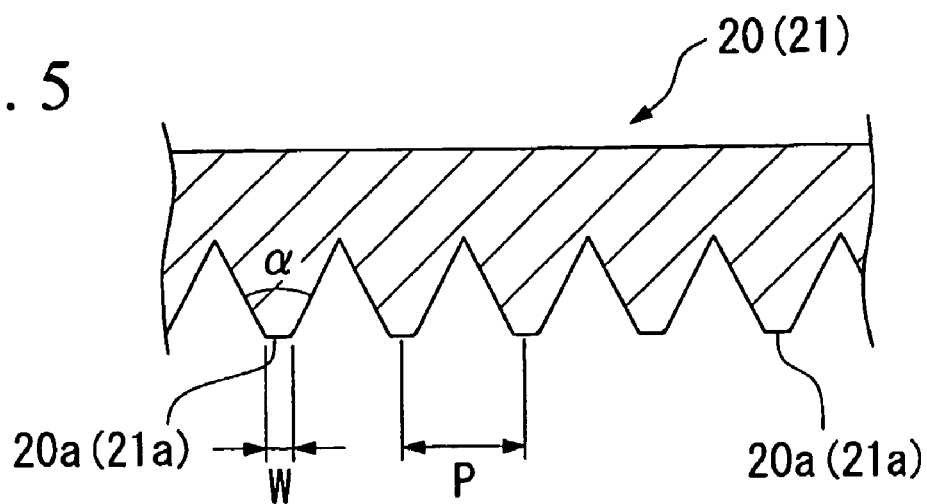
FIG. 5 is a cross-sectional view along V-V' in FIG. 4.

In the two heat seal bars 20 and 21 of FIG. 4, as seen in the enlarged view of FIG. 5, a plurality of projected streaks with a width W of 0.2 mm are formed as the seal edge 20a or 21a on the seal surface to run in parallel with each other at a distance P of 2 mm. These two heat seal bars 20 and 21 are disposed such that the projected streak seal edge 20a of one heat seal bar 20 and the projected streak seal edge 21a of another heat seal bar 21 are crossed at 90°, thereby sandwiching superposed two thermoplastic resin films.

As a result, the portion contacted and pressed from both surfaces of the thermoplastic resin film by seal edges 20a and 21a, respectively, becomes a strong melt-bonding part 15a having a small thickness and being strongly melt-bonded, and the portion not contacted from both surface sides by either the seal edge 20a or 21a of the heat seal bars 20 and 21 is heated indirectly by heat conduction or the like and becomes a weak melt-bonding part 15c which is weakly melt-bonded. The portion contacted only by the seal edge 20a or 21a of one heat seal bar 20 or 21 becomes a medium melt-bonding part 15b having a melt-bonding strength between the strong melt-bonding part 15a and the weak melt-bonding part 15c.

Accordingly, by using heat seal bars 20 and 21 where the width W, the distance P and depending on the case, the edge angle (which is described later) of seal edges are appropriately adjusted in advance such that the total area of the portions contacted and pressed from both surface sides of the thermoplastic resin film by seal edges 20a and 21a, respectively, is less than 25% of the entire weak seal part 15, a weak seal part 15 having a fixed opening strength can be easily formed.

Furthermore, according to such a method, even if the heat seal temperature is changed by about 1° C. from the optimal temperature, the opening strength of the obtained weak seal part 15 fluctuates only in the range of 1,000 N or less, preferably 750 N or less. Namely, the elevation rate of opening strength is 1,000 N/° C., preferably 750 N/° C. In practice, the opening strength is preferably on the order of 300 to 2,000 N, more preferably 300 to 1,500 N, and according to the method described above, even if the heat seal temperature slightly deviates, the opening strength readily falls in this range. The heat seal temperature may be appropriately determined according to the thermoplastic resin film used. The seal edge 20a or 21a which comprises a plurality of projected streaks formed to run nearly in parallel, preferably has a width W of 1 mm or less, more preferably 0.5 mm or less, and a distance P of 1 mm or more.

According to such a method, a weak seal part 15 having a desired opening strength can be formed only by using heat seal bars 20 and 21 where the width W, the distance P and depending on the case, the edge angle of the seal edge 20a or 21a are adjusted such that the total occupied area of the strong melt-bonding part 15a formed is less than 25% of the area of the weak seal part 15. Therefore, a strong seal step of liquid-tightly sealing the peripheral edge of the infusion container 10 with multiple chambers can be performed simultaneously with the weak seal step of forming the weak seal part 15 as such.

More specifically, heat seal bars (not shown) in the form capable of simultaneously sandwiching the peripheral edge of an infusion container 10 with multiple chambers, where the strong seal part 16 is formed, and the center part of the infusion container 10 with multiple chambers, where the weak seal part 15 is formed, are used, the seal edges 20a and 21a in the portion of forming the weak seal part 15 are adjusted, as described above, such that the total occupied area of the strong melt-bonding part 15a is less than 25%, and the seal edges in the portion of forming the strong seal part 16 are adjusted not to cause peeling of the seal part even when a force is applied to the medicament chamber 11 or 12, whereby the weak seal part 15 and the strong seal part 16 can be simultaneously formed only by one operation of sandwiching the thermoplastic resin films with heat seal bars.

As shown in FIG. 5, the edge angle α of the seal edge formed on the heat seal bar for forming the weak seal part 15 is preferably 120° or less. If the edge angle exceeds 120°, the area of the strong melt-bonding part 15 cannot be easily controlled. The edge angle is preferably 90° or less, more preferably 60° or less.

Figure 6A:
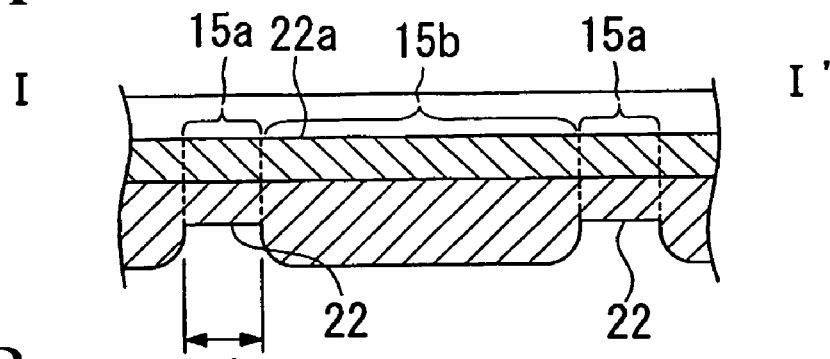
FIG. 6(a) is a cross-sectional view along I-I' in FIG. 3

As seen in FIGS. 6(a) and (b) which schematically show the cross-sectional views cut along the I-I' line and the II-II' line of FIG. 3, respectively, the thus-formed weak seal part 15a of the infusion container 10 with multiple chambers is in the state that a recessed part is formed resulting from the seal edge 20a or 21a of the heat seal bar 20 or 21 coming into contact with the thermoplastic resin film. In the case of this example, recessed streaks 22a having a width of about 0.2 mm or slightly larger than that and running in parallel at a distance of about 2 mm from each other are formed on both surfaces of the weak seal part 15 following the shape of the seal edge contacted. Among these recessed streaks 22a, some are the strong melt-bonding part 15a formed resulting from the seal edges 20a and 21a contact-pressing the thermoplastic resin film from both surface sides, and the remaining portions are the medium melt-bonding part 15b where the seal edge 20a or 21a comes into contact with the thermoplastic resin film only from one side.

The thus-formed recessed streak 22a is determined in correspondence with the width W or distance P of the seal edges 20a and 21a, however, the width W' shown is preferably about 1 mm or less and the distance P' is preferably about 1 mm or more. The width W' is liable to be the same as or slightly larger than the width W, and the distance P' is almost the same as the distance P.

Figure 2:
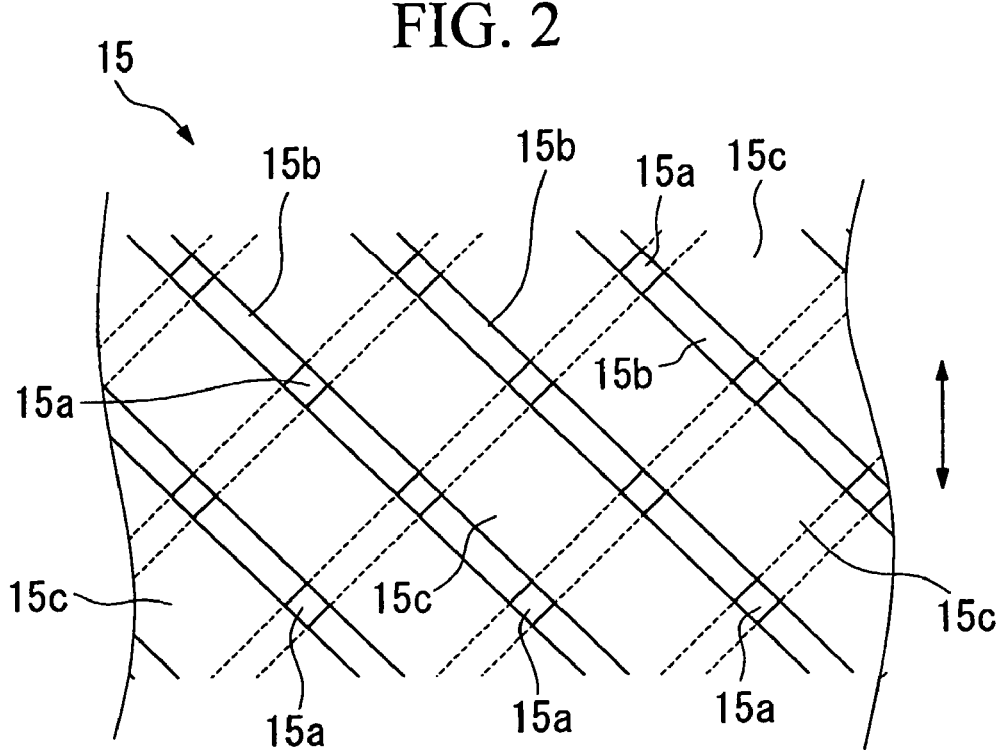
FIG. 2 is a partially enlarged plan view showing the weak seal part of the infusion container with multiple chambers of FIG. 1.

In this example, the recessed streak 22a is formed at an angle of 45° with respect to the longitudinal direction of the infusion container 10 with multiple chambers. This angle is not particularly limited but is preferably from 30 to 60°. In FIG. 2, the arrow direction is the longitudinal direction of the infusion container 10 with multiple chambers.

In this example, the strong melt-bonding part 15a is almost uniformly dispersed and distributed in the weak seal part 15 but as long as the total occupied area of the strong melt-bonding part 15a is less than 25% of the weak seal part 15, the distribution state thereof may be different in the cross direction of the weak seal part 15, namely, in the left to right direction in FIG. 1. For example, although not shown, it may be also possible that the strong melt-bonding part 15a is densely distributed in the vicinity of the center part in the cross direction and coarsely distributed in the vicinity of both edge parts in the cross direction or conversely, the strong melt-bonding part 15a is coarsely distributed in the vicinity of the center part in the cross direction and densely distributed in the vicinity of both edge parts in the cross direction.

By forming the strong melt-bonding part 15a to have a different distribution state in the cross direction of the weak seal part 15, the weak seal part 15 can be variously adjusted, for example, to provide the desired state at the peeling and opening or even when the infusion container 10 with multiple chambers falls by mistake and a force is applied to the edge part in the cross direction of the weak seal part 15, not to cause opening of the portion. In order to differentiate the distributed state of the strong melt-bonding part 15 as such, this may be attained by using a heat seal bar where a seal edge complying with such distribution is formed on the seal surface.

Second Embodiment

Figure 7:
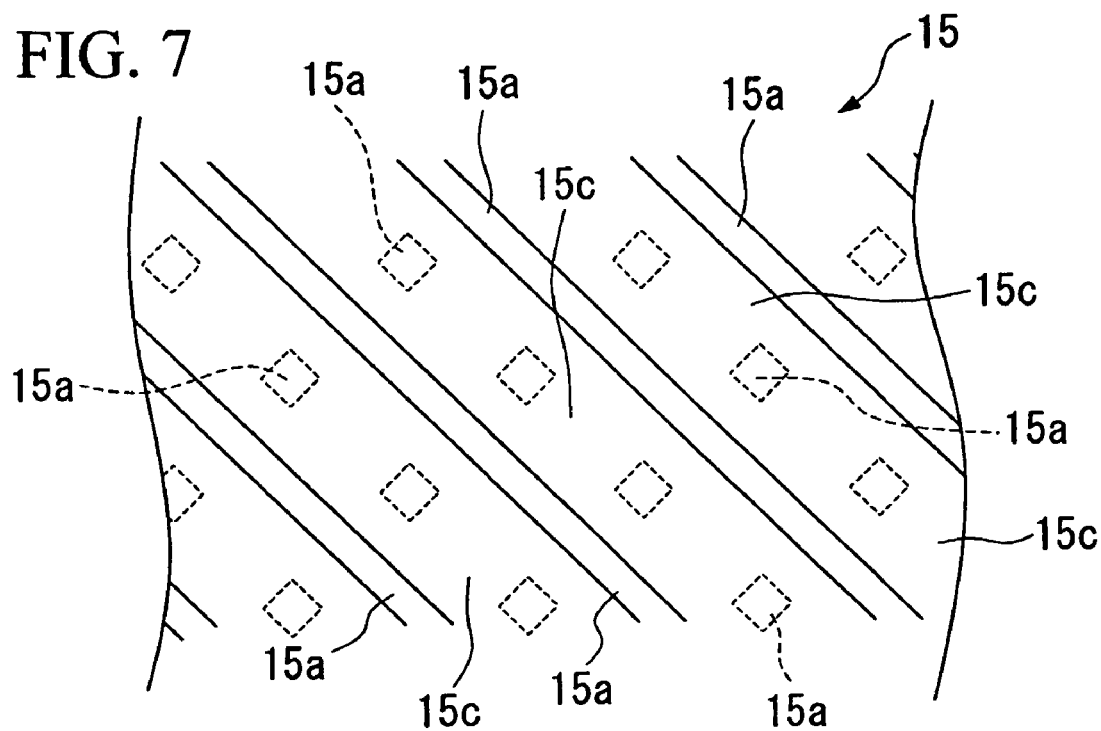
FIG. 7 is a partially enlarged plan view showing the weak seal part of the infusion container with multiple chambers according to another example of the present invention.

FIG. 7 shows the weak seal part 15 in an infusion container 10 with multiple chambers of the second embodiment.

The weak seal part 15 of this example is also formed by sandwiching superposed two thermoplastic resin films from both surface side by two heat seal bars each having a specific seal edge formed on the seal surface, and has two melt-bonding parts different in the melt-bonding strength, namely, a strong melt-bonding part 15a and a weak melt-bonding part 15c.

Among these, the strong melt-bonding part 15a having a high melt-bonding strength is formed to have a nearly square shape and a linear shape. The linear strong melt-bonding parts 15a are disposed in parallel with each other at equal intervals and between these, nearly square strong melt-bonding parts 15a are dispersed and distributed. The portions in the weak seal part 15 except for the strong melt-bonding part 15a all are the weak melt-bonding part 15c having a low melt-bonding strength.

Also in this example, the strong melt-bonding part 15a having a high peel strength out of those two kinds of melt-bonding parts is formed such that the total occupied area thereof is less than 25% of the entire area of the weak seal part 15, thereby appropriately controlling the opening strength of the weak seal part 15.

Furthermore, also in this example, respective strong melt-bonding parts 15a are dispersed and distributed in the weak seal part 15 such that the average space A and average distance B between adjacent strong melt-bonding parts 15a satisfy the relationship of formula (1). The average distance B is preferably 1 mm or more, more preferably 1.5 mm or more, still more preferably 2 mm or more. With this average distance, the opening strength of the weak seal part 15 can be unfailingly and very easily controlled.

Figure 8:
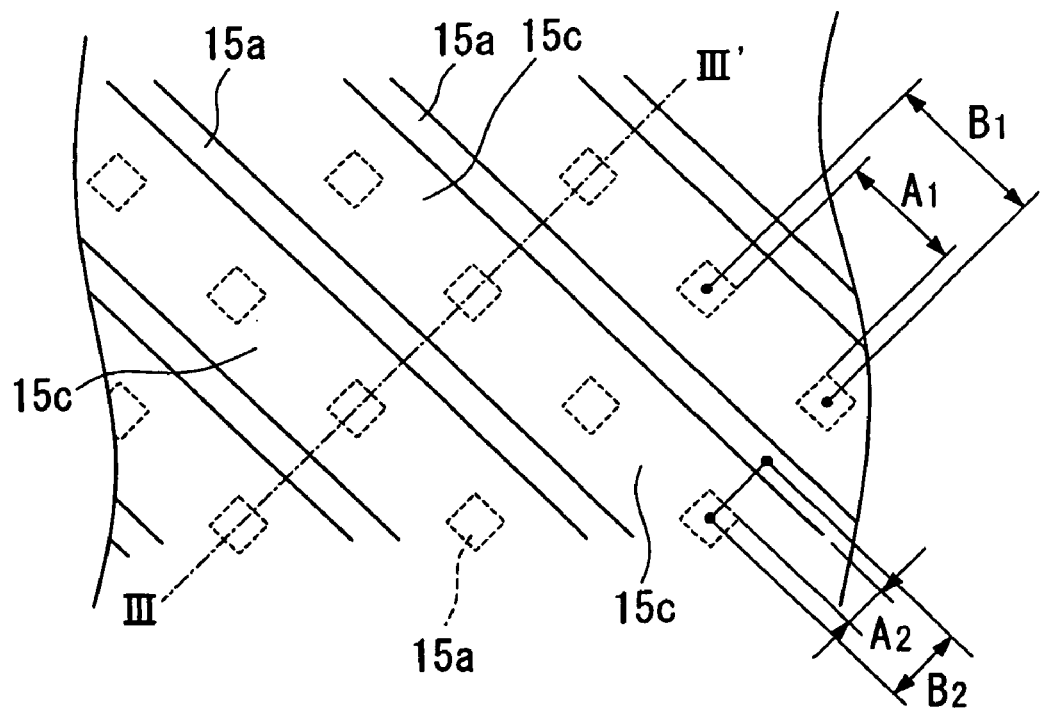
FIG. 8 is the same plan view as FIG. 7.

In this case, the space $A_1$ and distance $B_1$ between adjacent nearly square parts are determined as shown in FIG. 8 similarly to the first embodiment. On the other hand, the distance $B_2$ between a linear strong melt-bonding part 15a and a strong melt-bonding part 15a adjacent thereto having a planar shape such as nearly square shape is, when a perpendicular line is drawn from the centroid of the planar strong melt-bonding part 15a to the linear strong melt-bonding part 15a, a length between the above-described centroid and the center point in the cross direction of the linear strong melt-bonding part 15a on the perpendicular line. The space $A_2$ is a distance between the distal end of one strong melt-bonding part 15a and the distal end of another strong melt-bonding part 15a on the perpendicular line. The average space A and the average distance B are similarly determined by averaging these spaces or distances.

When the strong melt-bonding part 15a is formed to have a linear shape and a planar shape as such, the plane preferably has an area of 1 mm² or less and the line preferably has width of 1 mm or less. In the case of the planar shape, the shape is not limited to the nearly square form but may be other polygonal form or circular form.

Figure 9:
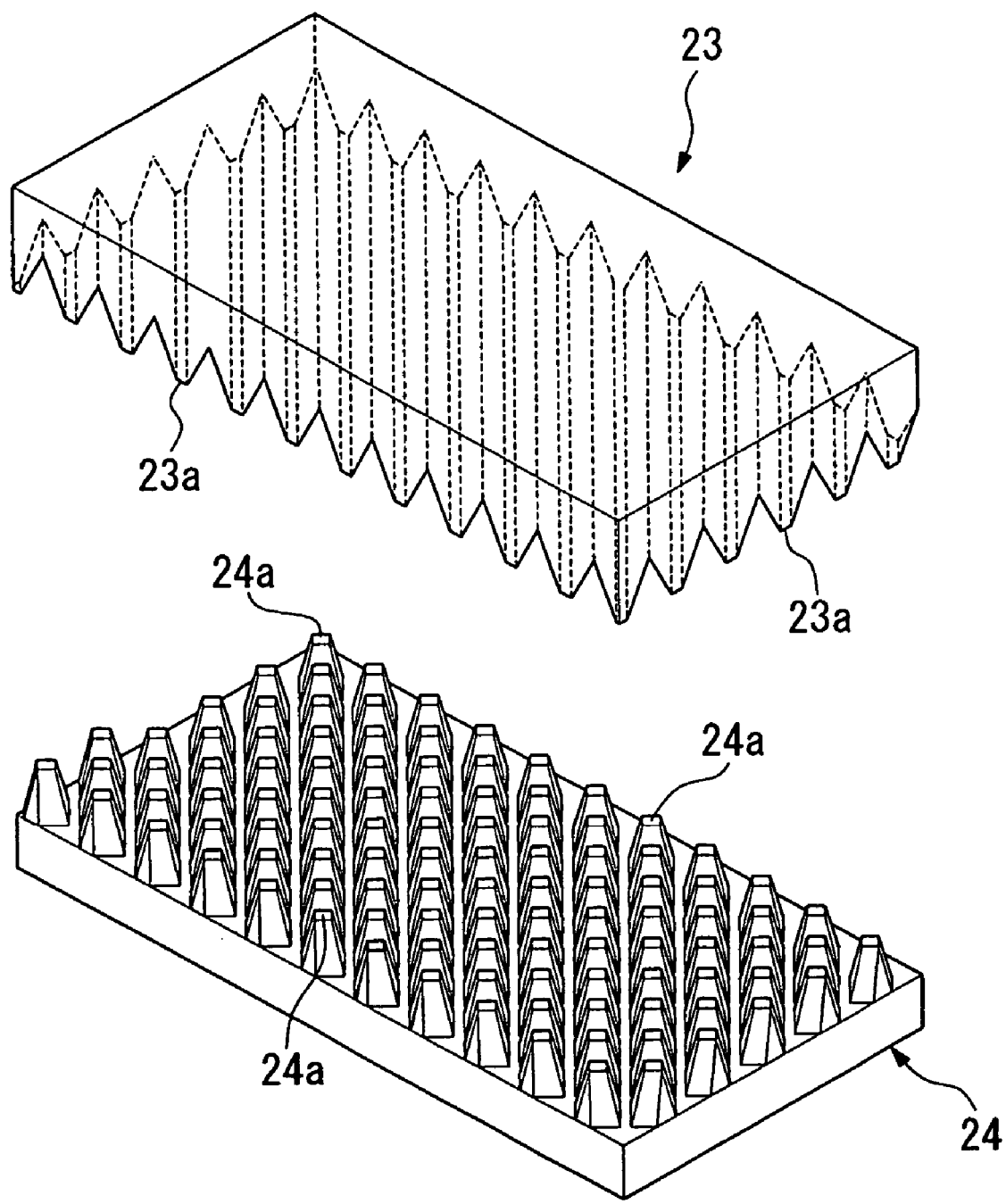
FIG. 9 is a perspective view of the heat seal bar used for forming the weak seal part of the infusion container with multiple chambers of FIG. 7.

This weak seal part 15 of the infusion container 10 with multiple chambers can be formed by sandwiching superposed two thermoplastic films from both surface sides using two heat seal bars 23 and 24 where a seal edge 23a or 24a as shown in FIG. 9 is formed on the seal surface.

Out of two heat seal bars 23 and 24 shown in FIG. 9, one heat seal bar 23 has a seal edge 23a as used in the first embodiment, which is obtained by forming a plurality of projected streaks to run in parallel with each other on the seal surface. Another heat seal bar 24 has a seal edge 24a which comprises a large number of nearly square projected planes distributed like a lattice at equal intervals. These heat seal bars sandwich the thermoplastic resin film such that the projected streak seal edge 23a of one heat seal bar 23 and the projected plane 24a of another heat seal bar 24 are dislocated from each other.

As a result, the portion contacted and pressed by the seal edge 23a or 24a from either one surface side of the thermoplastic resin film becomes a strong melt-bonding part 15a which is strongly melt-bonded, and the portion not contacted from both surface sides by either the seal edge 23a or 24a of the heat seal bars 23 and 24 is heated indirectly by heat conduction or the like and becomes a weak melt-bonding part 15c which is weakly melt-bonded.

Here, by using heat seal bars 23 and 24 where the width, distance and depending on the case, edge angle of each of the seal edges 23a and 24a are appropriately adjusted in advance such that the total of areas of the portions contacted and pressed from either one surface side of the thermoplastic resin film by seal edges 23a or 24a is less than 25% of the entire weak seal part 15, a weak seal part 15 having a fixed opening strength can be easily formed. In the case of using such heat seal bars 23 and 24, the width of the seal edge 23a which is a plurality of projected streaks formed almost in parallel is preferably 1 mm or less and the distance is preferably 1 mm or more. The area of the seal edge 24a which is a projected plane is preferably 1 mm² or less.

Figure 10:
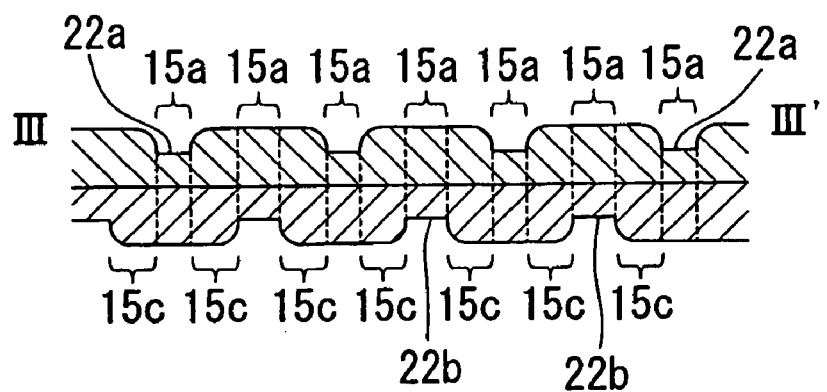
FIG. 10 is a cross-sectional view along III-III' in FIG. 8.

As seen in FIG. 10 showing the cross-sectional view cut along the III-III' line of FIG. 8, the thus-formed weak seal part 15a of the infusion container 10 with multiple chambers of this example is in the state that a recessed part is formed resulting from the seal edge 23a or 24a of the heat seal bar 23 or 24 coming into contact with the thermoplastic resin film. In the case of this example, the recessed part is formed on both surfaces of the weak seal part 15, more specifically, recessed streaks 22a are formed on one surface and nearly square recessed planes 22b are formed on another surface. The portion where the recessed streak 22a is formed and the portion where the recessed plane 22b is formed both are the strong melt-bonding part 15a.

The thus-formed recessed streak 22a corresponds to the width or distance of the seal edge of the heat seal bar used. The width is the same as or slightly greater than the width of the seal edge and the distance is almost the same as the distance of the seal edges. In the thus-formed recessed streak 22a, the width is 1 mm or less and the distance from each other is 1 mm or more. The area of the recessed plane 22b is almost the same as the area of the seal edge composed of a projected plane and is preferably 1 mm² or less.

Such a weak seal part 15 consisting of a strong melt-bonding part 15a and a weak melt-bonding part 15c can also be formed by using a film-made mold having higher heat resistance than the thermoplastic film used and having formed thereon holes corresponding to strong melt-bonding parts 15 to be formed. When the thermoplastic resin film is heated through this mold, the portions corresponding to the holes become the strong melt-bonding part 15a which is strongly melt-bonded, and other portions become the weak melt-bonding part 15c.

Third Embodiment

Figure 11:
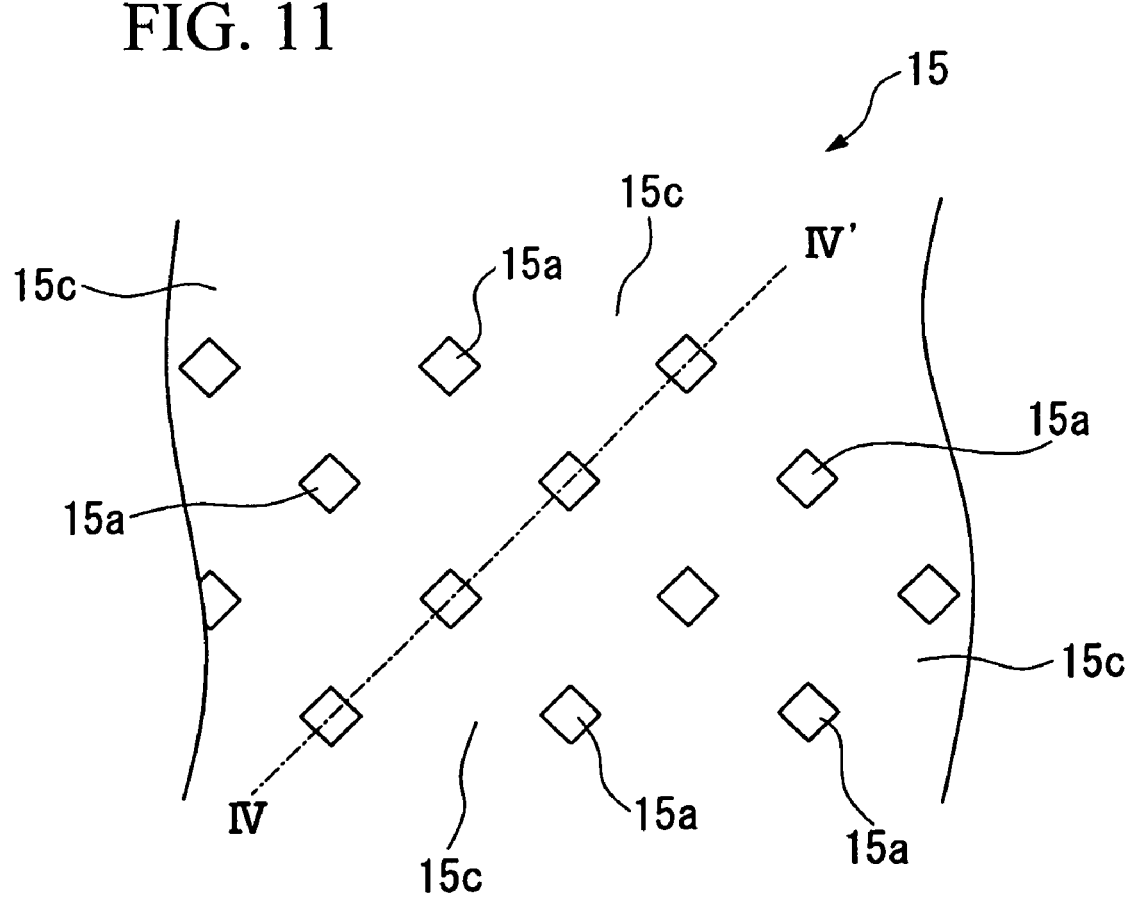
FIG. 11 is a partially enlarged plan view showing the weak seal part of the infusion container with multiple chambers according to another example of the present invention.

FIG. 11 shows the weak seal part 15 in an infusion container 10 with multiple chambers of the third embodiment.

The weak seal part 15 of this example is also formed by sandwiching superposed two thermoplastic resin films from both surface sides by two heat seal bars and has a strong melt-bonding part 15a and a weak melt-bonding part 15c.

Among these, the strong melt-bonding part 15a having a high melt-bonding strength is formed to have a nearly square shape. The portions in the weak seal part 15 except for the strong melt-bonding part 15a all are the weak melt-bonding part 15c having a low melt-bonding strength.

Also in this example, the strong melt-bonding part 15a is formed such that the total occupied area thereof is less than 25% of the entire area of the weak seal part 15, whereby the opening strength of the weak seal part 15 is appropriately controlled.

This weak seal part 15 of the infusion container 10 with multiple chambers can be formed by sandwiching superposed two thermoplastic films from both surface sides using a heat seal bar having a seal edge 24a comprising a large number of nearly square projected planes distributed like a lattice at equal intervals, shown by the numeral 24 in FIG. 9, and a heat seal bar having a planar seal surface (not shown) where a seal edge is not formed. The portion sandwiched and pressed by the seal edge 24a composed of a projected plane and the planar seal surface becomes the strong melt-bonding part 15a which is strongly melt-bonded, and the portion contacted from one surface side only by the planar seal surface of the heat seal bar becomes the weak melt-bonding part 15c.

Also in this case, when the heat seal bar is selected and used such that the total occupied area of the strong melt-bonding part 15a formed as above is less than 25% of the entire weak seal part 15, a stable weak seal part 15 having a fixed peel strength can be easily formed. In using such a heat seal bar, the area of the seal edge 24a composed of a projected plane is also preferably 1 mm$^2$ or less.

Figure 12:
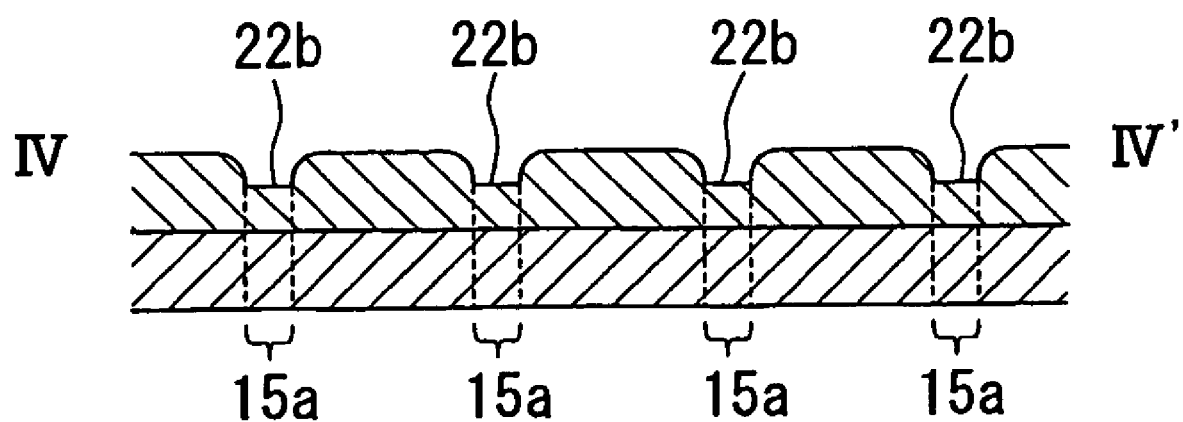
FIG. 12 is a cross-sectional view along IV-IV' in FIG. 11.

As seen in FIG. 12 showing the cross-sectional view cut along the IV-IV' line of FIG. 11, the thus-formed weak seal part 15 of the infusion container 10 with multiple chambers of this example is in the state that a recessed part, specifically, a recessed plane 22b is formed only on one surface resulting from the seal edge of the heat seal bar coming into contact with the thermoplastic resin film. In the case of this example, the recessed parts all are the strong melt-bonding part 15a.

When the recessed plane 22b is formed using a heat seal bar 24 having a seal edge 24a composed of a projected plane having an area of 1 mm$^2$ or less, the area thereof is also almost 1 mm$^2$ or less.

In forming the weak seal part 15 of this example, the strong melt-bonding part 15a and the weak melt-bonding part 15c can also be formed by the following method. The entire of the portion in which the weak seal part 15 is formed is sealed by a heat seal bar having a planar seal surface (not shown) where a seal edge is not formed, and this portion is further heated by a heat seal bar having a seal edge 24a comprising a large number of nearly square projected planes distributed like a lattice at equal intervals, shown by the numeral 24.

In these infusion containers 10 each having multiple chambers of first to third embodiments, the weak seal part 15 is particularly formed to have a plurality of melt-bonding parts different in the melt-bonding strength and the strong melt-bonding part 15a having a largest melt-bonding strength among these melt-bonding parts is dispersed and distributed in the weak seal part 15 and is controlled such that the total occupied area thereof is less than 25% of the area of the weak seal part 15, whereby the opening strength of the weak seal part 15 is appropriately controlled and the weak seal part thus formed can maintain the liquid-tight separation between the medicament chambers 11 and 12 at an ordinary time but when a force is externally applied to the medicament chamber 11 or 12, can be easily opened. Furthermore, even if the thermoplastic resin film used is a single layer film having crystallinity and is sealed at a temperature near the melting point thereof and also the heat sealing temperature is slightly changed, the dispersion in the opening strength of the weak seal part 15 can be suppressed to the minimum and an infusion container 10 with multiple chambers having a fixed performance can be stably produced.

EXAMPLES

The present invention is described in greater detail below by referring to Examples.

Example 1

A 300 μm-thick film comprising a linear low-density polyethylene (MFR: 2 g/10 min (190° C.), density: 0.925 g/cm$^3$, JIS K6760) was prepared by a water-cooling inflation method.

Two sheets of this film were superposed and sandwiched from both surface sides by two heat seal bars to form a peelable and openable weak seal part 15 and an unpeelable strong seal part 16, thereby producing an infusion container 10 with multiple chambers of the same type as shown in FIG. 1. At this time, the weak seal part 15 was formed to a length of 10 mm at the center part in the longitudinal direction of the infusion container 10 with multiple chambers. In the two heat seal bars used here, a large number of projected streak seal edges were formed almost in parallel as shown in FIG. 4 and the seal edge had a width W of 0.2 mm, a distance P of 2 mm and an edge angle α of 90°. The total occupied area of the strong melt-bonding part 15a in the weak seal part 15 was 4% in all cases.

Also, the sealing was performed under a sealing pressure of 0.39 MPa for a sealing time of 4 seconds at three kinds of heat sealing temperatures, namely, 118° C., 119° C. and 120° C. That is, three kinds of infusion containers 10 each having multiple chambers were produced, which were different only in the heat sealing temperature.

Thereafter, 1,000 ml of colored water in place of a medicament was filled in each of two medicament chambers 11 and 12 of respective infusion containers 10 with multiple chambers produced above and one medicament chamber 11 or 12 was pressed at a rate of 500 mm/minute by a plate of 100 mm×100 mm using a compression tester (RTC1250A, manufactured by Orientec). The load when the weak seal part 15 was opened was measured and used as the opening strength of the weak seal part 15.

As a result, the opening strength of the weak seal part 15 was 253N in the case of the infusion container 10 with multiple chambers produced at a heat sealing temperature of 118° C., 760N in the case of 119° C. and 1,267N in the case of 120° C. The elevation rate of the opening strength at 300 to 1,000N (change in the opening strength per 1° C.) was as small as 507 N/° C. and this reveals that the opening strength is not greatly changed even if the heat sealing temperature is slightly fluctuated.

Furthermore, 1,000 ml of colored water was filled in each of two medicament chambers 11 and 12 of respective infusion containers 10 with multiple chambers, each container was placed on a flat table, and both medicament chambers 11 and 12 were alternately pressed by hand 5 times in total. As a result, the weak seal part 15 was entirely peeled apart (when the weak seal part was entirely peeled apart within 5 times, the openability is shown by ○ in Table 1).

Figure 6B:
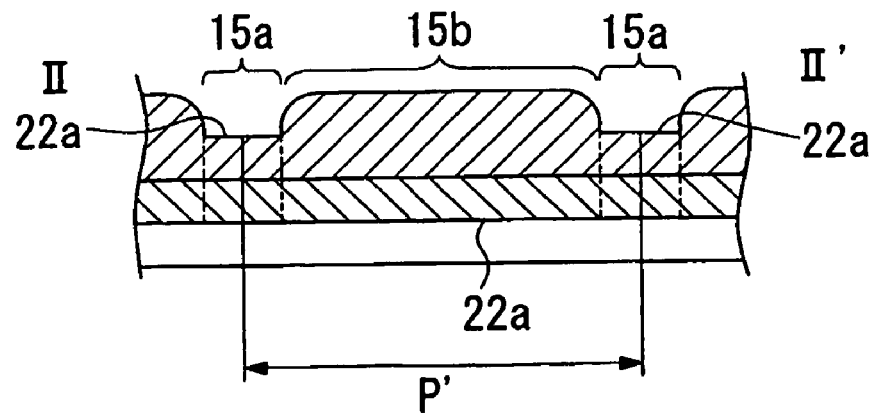
FIG. 6(b) is a cross-sectional view along II-II'.

In the weak seal part 15 of each infusion container 10 with multiple chambers, the width W' and distance P' (see FIG. 6) of the recessed streak were 2 mm and 0.4 mm, respectively, and the average space A and average distance B in formula (1) were 1.6 mm and 2 mm, respectively. These were measured by using a photograph of the weak seal part 15 taken at a magnification of 20 times.

These results and others are shown together in Tables 1 and 2.

Example 2

Three kinds of infusion containers 10 each having multiple chambers were produced in the same manner as in Example 1 except that the width W, distance P and edge angle α of the seal edge of two heat seal bars used were 0.2 mm, 4 mm and 90°, respectively, and temperatures of 120° C., 121° C. and 122° C. were used as the heat sealing temperature. In the weak seal part 15, the total occupied area of the strong melt-bonding part 15a was 0.6% in all cases.

These were evaluated in the same manner as in Example 1 and the results obtained are shown in Tables 1 and 2.

As seen from Table 2, the elevation rate of the opening strength was small at the opening strength of 300 to 1,000N and this reveals that the opening strength is not greatly changed even if the heat sealing temperature is slightly fluctuated. The openability was good.

Comparative Example 1

Two kinds of infusion containers 10 each having multiple chambers were produced in the same manner as in Example 1 except that the width W, distance P and edge angle α of the seal edge of two heat seal bars used were 0.4 mm, 1 mm and 90°, respectively, and temperatures of 117° C. and 118° C. were used as the heat sealing temperature. In the weak seal part 15, the total occupied area of the strong melt-bonding part 15a was 25% in either case.

These were evaluated in the same manner as in Example 1 and the results obtained are shown in Tables 1 and 2.

As seen from Table 2, the elevation rate of the opening strength was large at the opening strength of 300 to 1,000N and this reveals that the opening strength is greatly changed even if the heat sealing temperature is slightly fluctuated. The openability was bad (shown by X in Table 2) and a part of the weak seal part 15 was not peeled apart.

Comparative Example 2

Two kinds of infusion containers 10 each having multiple chambers were produced in the same manner as in Example 1 except that the width W, distance P and edge angle α of the seal edge of two heat seal bars used were 0.2 mm, 2 mm and 150°, respectively, and temperatures of 117° C. and 118° C. were used as the heat sealing temperature. In the weak seal part 15, the total occupied area of the strong melt-bonding part 15a was 30% in either case.

These were evaluated in the same manner as in Example 1 and the results obtained are shown in Tables 1 and 2.

As seen from Table 2, the elevation rate of the opening strength was large at the opening strength of 300 to 1,000N and this reveals that the opening strength is greatly changed even if the heat sealing temperature is slightly fluctuated. The openability was bad and a part of the weak seal part 15 was not peeled apart.

Example 3

Three kinds of infusion containers 10 each having multiple chambers were produced in the same manner as in Example 1 except that a heat seal bar having a seal edge comprising projected streaks as shown in FIG. 9, and a heat seal bar having a seal edge comprising projected planes (square projected planes were uniformly present like a lattice) were used in combination as the two heat seal bars, the seal edge in either form had a width W of 0.2 mm, a distance P of 4 mm and an edge angle α of 90°, and temperatures of 118° C., 119° C. and 120° C. were used as the heat sealing temperature. In the weak seal part 15, the total occupied area of the strong melt-bonding part 15a was 8% in all cases.

These were evaluated in the same manner as in Example 1 and the results obtained are shown in Tables 1 and 2.

As seen from Table 2, the elevation rate of the opening strength was small at the opening strength of 300 to 1,000N and this reveals that the opening strength is not greatly changed even if the heat sealing temperature is slightly fluctuated. The openability was good.

In Table 1, the average distance $A_1$ and the average distance $B_1$ were measured, as shown in FIG. 8, between strong melt-bonding parts 15a which are a recessed plane, and the average distance $A_2$ and the average distance $B_2$ were measured between a strong melt-bonding part 15a which is a recessed plane, and a strong melt-bonding part 15a which is a recessed streak.

Example 4

Three kinds of infusion containers 10 each having multiple chambers were produced in the same manner as in Example 1 except that a heat seal bar having a seal edge of the type shown by 24 in FIG. 9, which comprises (square) projected planes, and a heat seal bar with a planar seal surface not having a seal edge were used in combination as the two heat seal bars, the seal edge comprising projected planes had a width W of 0.2 mm, a distance P of 2 mm and an edge angle of 60°, and temperatures of 120° C., 121° C. and 122° C. were used as the heat sealing temperature. In the weak seal part 15, the total occupied area of the strong melt-bonding part 15a was 1% in all cases.

These were evaluated in the same manner as in Example 1 and the results obtained are shown in Tables 1 and 2.

As seen from Table 2, the elevation rate of the opening strength was small at the opening strength of 300 to 1,000N and this reveals that the opening strength is not greatly changed even if the heat sealing temperature is slightly fluctuated. The openability was good.

Comparative Example 3

Two kinds of infusion containers 10 each having multiple chambers were produced in the same manner as in Example 1 except that two heat seal bars each having a planar seal surface where a seal edge is not formed were used in combination and two kinds of temperatures, namely, 117° C. and 118° C., were used as the heat sealing temperature. In the weak seal part 15, the total occupied area of the strong melt-bonding part 15a was 100% in either case.

As seen from Table 2, the elevation rate of the opening strength was large at the opening strength of 300 to 1,000N and this reveals that the opening strength is greatly changed even if the heat sealing temperature is slightly fluctuated. The openability was bad and a part of the weak seal part 15 was not peeled apart.

TABLE 1

| | | | | | | Weak Seal Part of Infusion Container with Multiple Chambers | | |
|---|---|---|---|---|---|---|---|---|
| | | Heat Seal Bar | | | | Occupied Area of Strong | | |
| | P (mm) | W (mm) | α (mm) | P' (mm) | W' (mm) | Melt-Bonding Part (%) | B (mm) | A (mm) |
| Example 1 | 2 | 0.2 | 90 | 2 | 0.4 | 4 | 2 | 1.6 |
| Example 2 | 4 | 0.2 | 90 | 4 | 0.3 | 0.6 | 4 | 3.7 |
| Example 3 | 4 | 0.2 | 90 | 4 | 0.3 | 8 | 4($B_1$) 2($B_2$) | 3.7($A_1$) 1.7($A_2$) |
| Example 4 | 2 | 0.2 | 60 | 2 | 0.2 | 1 | 2 | 1.8 |

TABLE 1-continued

| | Heat Seal Bar | | | | | Weak Seal Part of Infusion Container with Multiple Chambers | | |
|---|---|---|---|---|---|---|---|---|
| | P (mm) | W (mm) | α (mm) | P' (mm) | W' (mm) | Occupied Area of Strong Melt-Bonding Part (%) | B (mm) | A (mm) |
| Comparative Example 1 | 1 | 0.4 | 90 | 1 | 0.5 | 25 | 1 | 0.5 |
| Comparative Example 2 | 2 | 0.2 | 150 | 2 | 1.1 | 30 | 2 | 0.9 |
| Comparative Example 3 | — | — | — | — | — | 100 | — | — |

TABLE 2

| | Opening Strength (N) at Each Sealing Temperature | | | | | | Elevation Rate of Opening | | |
|---|---|---|---|---|---|---|---|---|---|
| | 117 (°C.) | 118 (°C.) | 119 (°C.) | 120 (°C.) | 121 (°C.) | 122 (°C.) | Strength (N/°C.) | Liquid Leakage | Openability |
| Example 1 | | 253 | 760 | 1267 | | | 507 | ○ | ○ |
| Example 2 | | | | 501 | 771 | 1041 | 270 | ○ | ○ |
| Example 3 | | 321 | 850 | 1379 | | | 529 | ○ | ○ |
| Example 4 | | | | 366 | 633 | 900 | 267 | ○ | ○ |
| Comparative Example 1 | 630 | 1860 | | | | | 1230 | ○ | X |
| Comparative Example 2 | 540 | 1640 | | | | | 1100 | ○ | X |
| Comparative Example 3 | 720 | 1900 | | | | | 1180 | ○ | X |

After a liquid was filled in the medicament chambers 11 and 12, leakage of the liquid into the weak seal part 15 was not observed with an eye in all of the infusion containers 10 with multiple chambers, obtained in Examples 1 to 4 and Comparative Examples 1 to 3.

INDUSTRIAL APPLICABILITY

As described in the foregoing pages, in the infusion container with multiple chambers of the present invention, the total occupied area of the strong melt-bonding part in the weak seal part is less than 25%, so that the peel strength of the boundary portion between one and another of multiple medicament chambers is stabilized irrespective of the construction material and structure of the film. Furthermore, according to the production method of the present invention, such an infusion container with multiple chambers can be easily produced with good productivity.

The invention claimed is:

1. An infusion container with multiple chambers, which is formed from a thermoplastic resin film and has a plurality of medicament chambers for housing medicaments, wherein
the medicament chambers are liquid-tightly sealed by a peelable weak seal part which consists of a thermoplastic resin,
said weak seal part is formed to have a plurality of melt-bonding parts different in the melt-bonding strength,
the strong melt-bonding part having a largest melt-bonding strength among said melt-bonding parts is dispersed and distributed in said weak seal part,
the total occupied area of the strong melt-bonding part is less than 25% of the area of said weak seal part, and
the peelable weak seal part of the thermoplastic resin film is free from a coating material-applied part.

2. The infusion container with multiple chambers as claimed in claim 1, wherein respective strong melt-bonding parts are distributed such that the average space A and average distance B between adjacent strong melt-bonding parts satisfy the following formula $$B < 2A \quad (1).$$

3. The infusion container with multiple chambers as claimed in claim 2, wherein said average distance B between strong melt-bonding parts is 1.0 mm or more.

4. The infusion container with multiple chambers as claimed in claim 1, wherein each strong melt-bonding part is a plane having an area of 1 mm$^2$ or less and/or a line having a width of 1 mm or less.

5. The infusion container with multiple chambers as claimed in any one of claims 1 to 4, wherein at least one surface of the weak seal part has a recessed part and at least a part of said recessed parts are the strong melt-bonding part.

6. The infusion container with multiple chambers as claimed in claim 5, wherein said recessed part comprises a plurality of recessed streaks formed almost in parallel and each having a width of 1 mm or less and/or a plurality of recessed planes each having an area of 1 mm$^2$ or less.

7. The infusion container with multiple chambers as claimed in claim 5, wherein one surface of the weak seal part has the recessed part and another surface is planarly formed.

8. The infusion container with multiple chambers as claimed in claim 5, wherein both surfaces of the weak seal part have the recessed part.

9. The infusion container with multiple chambers as claimed in any one of claims 1 to 4, wherein the dispersed state of respective strong melt-bonding parts is different in the cross direction of the weak seal part.

10. The infusion container with multiple chambers as claimed in claim 5, wherein the dispersed state of respective strong melt-bonding parts is different in the cross direction of the weak seal part.

11. The infusion container with multiple chambers as claimed in claim 7, wherein the dispersed state of respective strong melt-bonding parts is different in the cross direction of the weak seal part.

12. The infusion container with multiple chambers as claimed in claim 8, wherein the dispersed state of respective strong melt-bonding parts is different in the cross direction of the weak seal part.

* * * * *